US006171293B1

(12) United States Patent
Rowley et al.

(10) Patent No.: US 6,171,293 B1
(45) Date of Patent: Jan. 9, 2001

(54) VENTING DEVICES

(75) Inventors: Peter Rowley; Ray Summers, both of Stroud (GB)

(73) Assignee: Sterimatic Holdings Limited, Gloucestershire (GB)

( * ) Notice: Under 35 U.S.C. 154(b), the term of this patent shall be extended for 0 days.

(21) Appl. No.: 09/180,467

(22) PCT Filed: May 7, 1997

(86) PCT No.: PCT/GB97/01235

§ 371 Date: Nov. 9, 1998

§ 102(e) Date: Nov. 9, 1998

(87) PCT Pub. No.: WO97/42305

PCT Pub. Date: Nov. 13, 1997

(30) Foreign Application Priority Data

May 8, 1996 (GB) .................................................. 9609563

(51) Int. Cl.[7] ..................................................... A61B 19/00
(52) U.S. Cl. ........................................... 604/403; 604/411
(58) Field of Search ..................................... 604/403, 405, 604/408, 411, 412, 414, 415; 206/219, 221, 222

(56) References Cited

U.S. PATENT DOCUMENTS 4,507,118 3/1985 Dent .
4,524,809 6/1985 Dent .
4,552,277 11/1985 Richardson et al. .
5,423,793 * 6/1995 Isono et al. .......................... 604/410
5,776,124 * 7/1998 Wald .................................... 604/403
5,785,701 * 7/1998 Sams et al. .......................... 604/411
5,873,872 * 2/1999 Thibault et al. ..................... 604/414
5,895,383 * 4/1999 Niedospial, Jr. ..................... 604/403

* cited by examiner

*Primary Examiner*—Glenn K. Dawson
*Assistant Examiner*—David J. Cho
(74) *Attorney, Agent, or Firm*—Young & Thompson

(57) ABSTRACT

A venting device is provided for venting the interior of a blood culture bottle by passing the tip of a hollow needle through a sealing stopper of the bottle. The device includes a collapsible shield for shielding the needle, a needle support in the vicinity of one end of the shield for holding the needle and incorporating a vent passage providing fluid communication between the hollow interior of the needle and the atmosphere, and a detachable sterilizing cap on the other end of the shield. The two ends of the shield are reciprocable relative to one another in the direction of the length of the needle against the action of a compression spring. Venting of the bottle is effected by placing the end of the shield against the sealing stopper with the shield in an extended condition, and applying pressure to the device in a direction towards the sealing stopper. This causes the tip of the needle to move through the sterilizing cap and to pass through the sealing stopper to vent the bottle as the shield collapses under the applied pressure. In use of such a venting device for venting of a blood culture bottle, the needle is sterilized and the venting operation is effected in a single movement, so that a large number of venting operations may be carried out in a short space of time.

14 Claims, 2 Drawing Sheets

VENTING DEVICES

This invention relates to venting devices of the kind provided for venting the interior of a sealed container by passing the tip of a hollow needle through a sealing portion of the container.

In the laboratory testing of blood samples, it is conventional practice for the blood samples to be contained in blood culture bottles of standard type provided with self-sealing rubber stoppers. Samples of blood may be introduced into, and removed from, the bottles by passing the needle of a syringe through the stopper and either dispensing the blood sample from the syringe or drawing the blood sample into the syringe, the bottle being automatically resealed on withdrawal of the needle from the stopper. In certain laboratory tests, it is necessary for cultures to be grown aerobically, and this requires the introduction of air into the blood culture bottles. This may be achieved by injecting air through the bottle stopper using a conventional syringe, or alternatively by simply passing an open-ended hollow needle through the stopper to permit venting of the interior of the bottle.

WO 94/19451 discloses a venting device for a culture bottle in which a needle carrier is axially slidable in a guide tube so as to penetrate the bottle septum with the object of releasing pressure built up in the bottle due to organism growth. Such a device enables the asepticty of the needle to be maintained substantially right up to the moment of penetration of the bottle septum. The venting device is preferably in the form of a sterile package which is disposable after use.

Known methods of introducing air into such blood culture bottles suffer from a number of disadvantages in use. Firstly it is necessary for the needle to be replaced after puncturing of each bottle stopper in order to prevent cross-contamination between blood samples. Furthermore there is a danger that the operator will be accidentally pricked with the needle of the syringe on removal of the needle from the bottle stopper. As is well known, so-called "needle stick" can be highly dangerous due to the risk of transfer of blood-related diseases.

U.S. Pat. No. 4,507,118 discloses a fitment for an animal injection gun incorporating a collapsible sleeve and sterilising means at the end of the sleeve which serves to sterilise the tip of the needle of the injection gun during an injection so that a large number of animals can be injected using a single fitment without risk of cross-infection.

BRIEF DESCRIPTION OF THE INVENTION

It is an object of the invention to provide a venting device which overcomes one or more of these disadvantages.

According to the present invention there is provided a venting device for venting the interior of a sealed container by passing the tip of a hollow needle through a sealing portion of the container, the device comprising a collapsible shield for shielding the needle, a needle support in the vicinity of one end of the shield for holding the needle and incorporating a vent passage providing fluid communication between the hollow interior of the needle and the atmosphere, and sterilising means in the vicinity of the other end of the shield, the two ends of the shield being reciprocable relative to one another in the direction of the length of the needle, whereby, in use, when venting of the container is effected by placing said other end of the shield against the sealing portion with the shield in an extended condition and applying pressure to the device in a direction towards the sealing portion, the tip of the needle moves through the sterilising means and passes through the sealing portion to vent the container as the shield collapses under the applied pressure.

In use of such a venting device for venting of a blood culture bottle, the needle is sterilised and the venting operation is effected in a single movement, so that a large number of venting operations may be carried out in a short space of time. Optionally a plurality of such devices may be mounted in a jig permitting venting of a plurality of containers simultaneously, so as to render the device particularly easy to use in such a manner as to enable a large number of venting operations to be carried out whilst allowing sufficient time for the sterilising action to take place during the venting operation. Whilst the word "sterilising" is used in this specification in the sense of killing microorganisms, such as bacteria or viruses, it should be understood that it is not essential that all microorganisms are killed, that is to say that the needle is rendered absolutely sterile. Furthermore it is to be understood that the word "shield" includes arrangements in which the wall of the shield is either continuous or apertured (in which case the apertures may be in the form of slots extending from one end of the sleeve to the other).

Advantageously the vent passage incorporates a vent filter for cleaning of air passing along the vent passage.

Furthermore the vent passage may include an axial passage aligned with the needle and opening into a chamber, and a transverse passage extending from the chamber and opening to atmosphere at an outer surface of the device.

Preferably the shield is resiliently biased into its extended condition, for example by means of a spring within the shield, so that, on release of the applied pressure after venting of the container, the tip of the needle moves back through the sterilising means as the shield reassumes its extended condition.

Furthermore the sterilising means is preferably disposed adjacent but beyond the tip of the needle when the shield is in its extended condition so that the tip of the needle enters and moves through the sterilising means as the shield collapses under applied pressure.

The sterilising means may comprise a holder for locating a sterilising substance in the vicinity of said other end of the shield, the holder being detachable from the shield.

Advantageously the sterilising means may include a body of absorbent material for impregnation with a sterilising substance. The sterilising means may include an enclosure having an end wall which is adapted to have an integral removable portion separated therefrom by rupturing the material of the end wall in a predetermined region so as to form an aperture in the end wall through which the tip of the needle may pass. Alternatively or additionally the enclosure may have an end wall which is simply adapted to be punctured by the needle as the tip of the needle moves through the sterilising means.

The invention also provides a venting device for venting the interior of a sealed container by passing the tip of a hollow needle through a sealing portion of the container, the device comprising a needle support for holding the needle and incorporating a vent passage providing fluid communication between the hollow interior of the needle and the atmosphere, and a needle guard coupled to the needle support and extending in the direction of the length of the needle to a position beyond the tip of the needle, the needle guard permitting venting of the container by passing the tip of the needle through the sealing portion of the container whilst shielding the tip of the needle to prevent accidental needle stick when the tip of the needle is removed from the container.

BRIEF DESCRIPTION OF THE SEVERAL VIEWS OF THE DRAWING

In order that the invention may be more fully understood, preferred embodiments of the invention will now be described, by way of example, with reference to the accompanying drawing, in which.

DETAIL DESCRIPTION OF THE INVENTION

Figure 1:
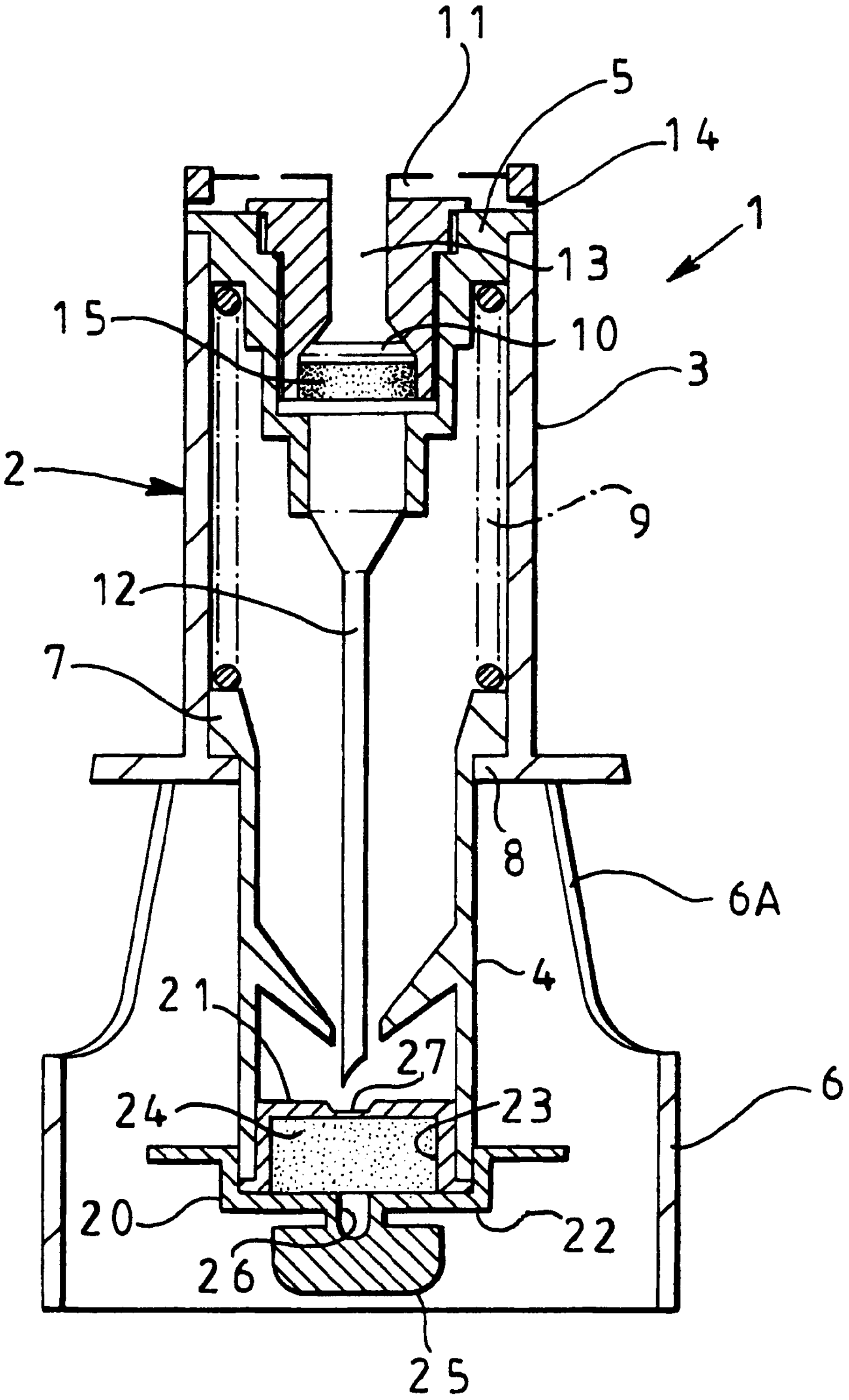
FIG. 1 is a diagrammatic view of a first embodiment in axial section.

The venting device 1 of FIG. 1 comprises a collapsible sleeve 2 in the form of two telescoping tubes 3 and 4, the outer tube 3 of which may be fixedly attached to a needle support 5 and has a generally tubular needle shroud 6 depending therefrom which is provided with finger holes 6A therein at diametrically opposite locations. The inner tube 4 of the sleeve 2 is held within the outer tube 3 by an outer annular flange 7 on the inner tube 4 engaging an inner annular flange 8 on the outer tube 3. Furthermore a compression spring 9 within the outer tube 3 acts on the flange 7 so as to bias the inner tube 4 outwardly so that the sleeve 2 is in its extended condition shown in the drawing in the absence of an applied force acting on the end of the sleeve 2 in such a manner as to compress the sleeve 2.

In a non-illustrated embodiment, the needle support S is adapted to be detachably connected to a needle connecting body of a multidose injection gun in which case a range of adaptors may be provided for fitting to different types of gun. However the venting device 1 is not adapted for fitting to an injection gun in the illustrated embodiment.

The needle support 5 is provided with a connector part 10 to which a hollow needle 12 is fixedly or detachably fitted. The needle support 5 is additionally provided with a vent chamber 11 which is in fluid communication with the hollow interior bore of the needle 12 by way of an axial passage 13 aligned with the needle 12 and opening into the chamber 11. The vent chamber 11 is open to atmosphere at the top of the needle support 5, and additionally transverse holes 14 extend from the chamber 11 through the sides of the needle support 5 to enable air to be sucked in even when the top of the chamber 11 is closed off by the user's finger. An air filter 15 is provided to clean air passing from the vent chamber 11 into the interior bore of the needle 12.

A detachable sterilising cap 20 on the end of the sleeve 2 comprises a cup-shaped body part 21 and a cover part 22 fitted thereto so as to provide an enclosure 23 for a sponge 24 impregnated with a sterilising liquid. The cover part 22 has a twist-off portion 25 which may be twisted to separate it from the remainder of the cover part 22, thereby leaving an aperture 26 in the cover part 22. The body part 21 has a weakened region 27 designed to be punctured by the tip of the needle 12 prior to passing through the sponge 24 and exiting from the enclosure 23 by way of the aperture 26 formed by removal of the twist-off portion 25.

In use of the venting device 1 to vent a blood culture bottle, the sterilising cap 20 is fitted to the sleeve 2 and the twist-off portion 25 removed therefrom. The shroud 6 is then fitted over the neck of the bottle so that the sterilising cap 20 engages the rubber stopper of the bottle. Pressure is then applied to the device 1 in the direction towards the rubber stopper so as to cause the sleeve 2 to be contracted on movement of the inner tube 4 inwardly of the outer tube 3 against the action of the spring 9. This results in piercing of the weakened portion 27 of the sterilising cap 20 by the tip of the needle 12 and movement of the tip of the needle 12 through the sponge 24, the needle tip exiting from the sterilising cap 20 by way of the aperture 26 and puncturing the rubber stopper so as to enter the interior of the bottle. This results in air being drawn by way of the vent chamber 11, the axial passage 13, the air filter 15 and the interior bore of the needle 12 into the bottle under vacuum pressure.

After completion of the venting operation, the applied pressure is removed from the device 1 permitting the sleeve 2 to reassume its extended position under the action of the spring 9. This results in the tip of the needle 12 being withdrawn from the bottle stopper and passing back through the sterilising cap 20 so as to return to the position shown in the figure. The bottle stopper is automatically re-sealed on retraction of the needle so as to prevent contamination of the contents of the bottle. The action of moving the tip of the needle 12 through the sponge 24 impregnated with sterilising liquid causes the tip of the needle 12 to be coated with a layer of sterilising liquid and additionally wipes the outer surface of the needle 12. Thus the tip 12 of the needle is sterilised both as it is passed into the bottle stopper and as it is subsequently withdrawn from the bottle stopper. This therefore-prevents contamination of the bottle contents by the introduction of the tip of the needle 12 into the bottle, and additionally serves to sterilise the tip of the needle 12 after it has been withdrawn from the bottle in which it will possibly have become contaminated with blood.

Furthermore, when the device 1 has been removed from a blood culture bottle after venting of the bottle, the needle shroud 6 serves to prevent needle stick by virtue of the fact that the needle tip will not extend beyond the end of the shroud 6 even if pressure is accidentally exerted on the device 1 so as to contract the sleeve 2 and cause the needle tip to pass through the sterilising cap 20.

The above described arrangement may be used for venting a number of blood culture bottles consecutively without requiring replacement of either the venting device 1 or the sterilising cap 20. However it is envisaged that the sterilising cap 20 will be replaced by a fresh sterilising cap after a number of venting operations have been completed, or after a certain length of time has taken place since the last venting operation. Furthermore, since the venting device 1 will eventually become unacceptably contaminated after a certain number of venting operations or after a certain period of use, it is envisaged that the venting device 1 will eventually require replacement by a fresh venting device.

Figure 2:
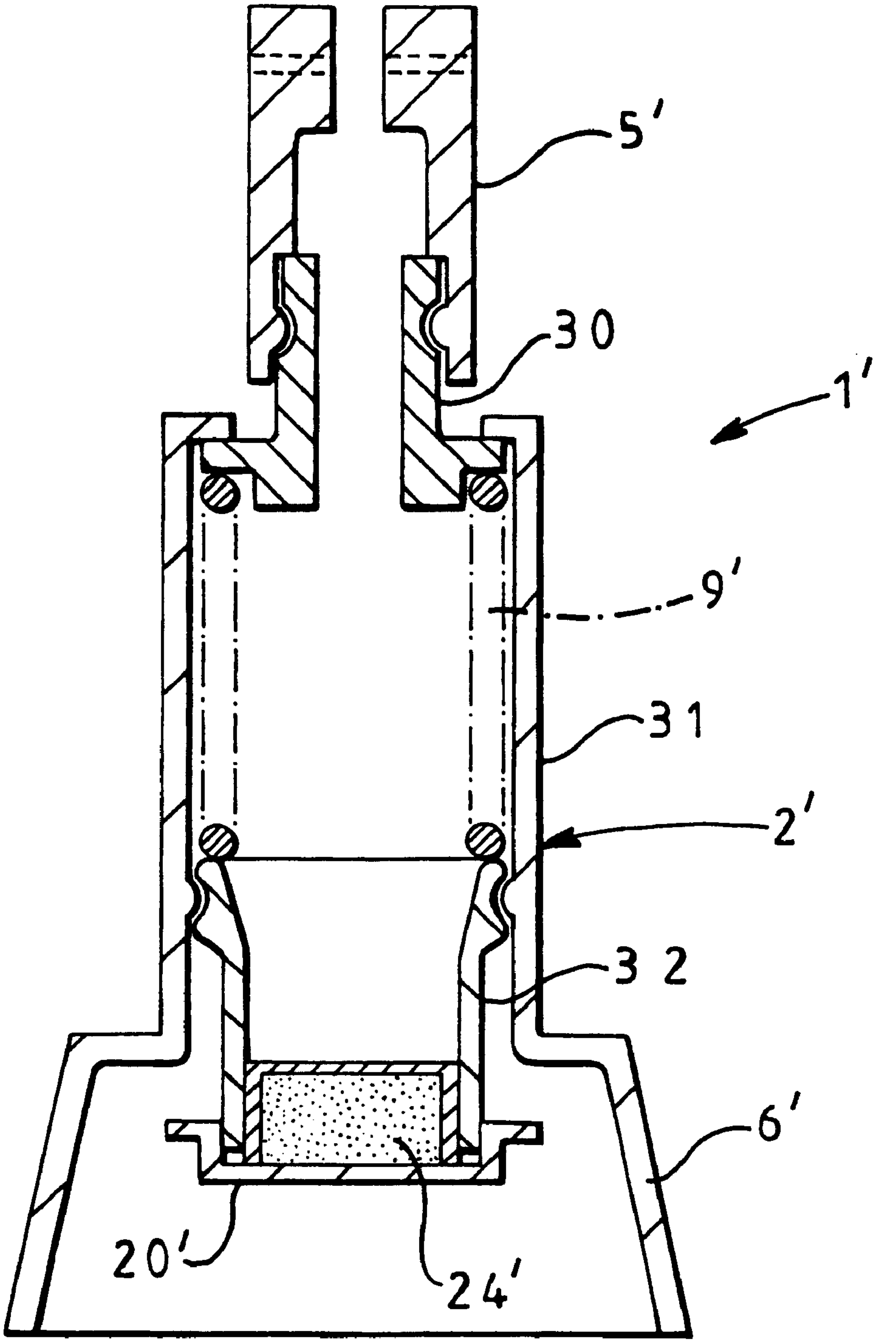
FIG. 2 is a diagrammatic view of a second embodiment in axial section, with the needle omitted.

FIG. 2 shows a venting device 1' in accordance with an alternative embodiment of the invention. It should be noted that the needle is omitted from the figure, although it will be understood that a similar needle is provided in this embodiment to the needle 12 as shown in FIG. 1. Furthermore the same numerals are used as in FIG. 1, but with primes added, to denote similar parts. However, in the embodiment of FIG. 2, instead of the needle being fixed relative to the needle shroud 6', the needle is axially movable relative to the shroud 6' so as to enable the needle tip to pass through the sterilising cap 20'.

More particularly the venting device 1' of FIG. 2 comprises a collapsible sleeve 2' in the form of two telescoping tubes 30 and 31, the inner tube 30 of which is detachably connectible to a needle support 5' and the outer tube 31 of which has the needle shroud 6' depending therefrom, as well as a detachable inner holder 32. In use of the venting device 1' to vent a blood culture bottle, the sterilising cap 20' is fitted to the holder 32 and the shroud 6' is fitted over the neck of the bottle so that the sterilising cap 20' engages the rubber stopper of the bottle. Pressure is then applied to the needle support 5' in the direction towards the rubber stopper so as to cause the inner tube 30 and the needle projecting therefrom to move within the outer tube 31 against the action of the spring 9', thus causing the needle tip to pass through the sterilising cap 20' into the rubber stopper and the interior of the bottle. It should be noted that the sterilising cap 20' is shown without a twist-off portion in FIG. 2 to show that the provision of such a twist-off portion is not essential, and it is possible for the needle to simply puncture both walls of the sterilising cap 20'. An advantage of the embodiment of FIG. 2 is that the sterilising cap 20' can be replaced by a fresh cap with substantially no danger of the user being pricked by the needle during fitting of the cap to the holder 32.

What is claimed is:

1. A venting device for venting the interior of a sealed container by passing the tip of a hollow needle through a sealing portion of the container, the device comprising a collapsible shield (2) for shielding the needle (12), a needle support (5) in the vicinity of one end (3) of the shield for holding the needle (12) and incorporating a vent passage providing fluid communication between the hollow interior of the needle (12) and the atmosphere, and sterilizing means (20) in the vicinity of the other end (4) of the shield (2), the two ends (3, 4) of the shield (2) being reciprocable relative to one another in the direction of the length of the needle (12), whereby, in use, when venting of the container is effected by placing said other end (4) of the shield (2) against the sealing portion with the shield (2) in an extended condition and applying pressure to the device in a direction towards the sealing portion, the tip of the needle (12) moves through the sterilizing means (20) and passes through the sealing portion to vent the container as the shield (2) collapses under the applied pressure.

2. A venting device according to claim 1, wherein the vent passage incorporates a vent filter (15) for cleaning of air passing along the vent passage.

3. A venting device according to claim 1, wherein the vent passage includes an axial passage (13) aligned with the needle (12) and opening into a chamber (11), and a transverse passage (14) extending from the chamber (11) and opening to atmosphere.

4. A venting device according to claim 1, wherein the shield (2) is resiliently biased into its extended condition by means of a spring (9) so that, on release of the applied pressure after venting of the container, the tip of the needle (12) moves back through the sterilizing means (20) as the shield (2) reassumes its extended condition.

5. A venting device according to claim 1, wherein the sterilizing means (20) is disposed adjacent but beyond the tip of the needle (12) when the shield (2) is in its extended condition so that the tip of the needle (12) enters and moves through the sterilizing means (20) as the shield (2) collapses under applied pressure.

6. A venting device according to claim 1, wherein the sterilizing means comprises a holder (20) for locating a sterilizing substance in the vicinity of said other end (4) of the shield (2), the holder (20) being detachable from the shield (2).

7. A venting device according to claim 1, wherein the sterilizing means (20) includes a body (24) of absorbent material for impregnation with a sterilizing substance.

8. A venting device according to claim 1, wherein the sterilizing means (20) includes an enclosure (23) having an end wall (22) which is adapted to have an integral removable portion (25) separated therefrom by rupturing the material of the end wall (22) in a predetermined region so as to form an aperture (26) in the end wall (22) through which the tip of the needle (12) may pass.

9. A venting device according to claim 1, wherein the sterilizing means (20) includes an enclosure (23) having an end wall (21) which is adapted to be punctured by the needle (12) as the tip of the needle (12) moves through the sterilizing means (20).

10. A venting device according to claim 1, wherein said other end (4) of the shield (2) is shaped to engage a neck of the container.

11. A venting device for venting the interior of a sealed container by passing the tip of a hollow needle through a sealing portion of the container, the device comprising a collapsible shield (2) for shielding the needle (12), a needle support (5) in the vicinity of one end (3) of the needle for holding the needle (12) and incorporating a vent passage providing fluid communication between the hollow interior of the needle (12) and the atmosphere and incorporating a vent filter (15) for cleaning of air passing along the vent passage, and sterilizing means (20) in the vicinity of the other end (4) of the shield (2), the two ends (3, 4) of the shield (2) being reciprocable relative to one another in the direction of the length of the needle (12), whereby, in use, when venting of the container is effected by placing said other end (4) of the shield (2) against the sealing portion with the shield (2) in an extended condition and applying pressure to the device in a direction towards the sealing portion, the tip of the needle (12) moves through the sterilizing means (20) and passes through the sealing portion to vent the container as the shield (2) collapses under the applied pressure.

12. A venting device for venting the interior of a sealed container by passing the tip of a hollow needle through a sealing portion of the container, the device comprising a collapsible shield (2) for shielding the needle (12), a needle support (5) in the vicinity of one end (3) of the needle for holding the needle (12) and incorporating a vent passage providing fluid communication between the hollow interior of the needle (12) and the atmosphere, the vent passage including an axial passage (13) aligned with the needle (12) and opening into a chamber (11) and a transverse passage (14) extending from the chamber (11) and opening to atmosphere, and sterilizing means (20) in the vicinity of the other end (4) of the shield (2), the two ends (3, 4) of the shield (2) being reciprocable relative to one another in the direction of the length of the needle (12), whereby, in use, when venting of the container is effected by placing said other end (4) of the shield (2) against the sealing portion with the shield (2) in an extended condition and applying pressure to the device in a direction towards the sealing portion, the tip of the needle (12) moves through the sterilizing means (20) and passes through the sealing portion to vent the container as the shield (2) collapses under the applied pressure.

13. A venting device for venting the interior of a sealed container by passing the tip of a hollow needle through a sealing portion of the container, the device comprising a collapsible shield (2) for shielding the needle (12), a needle support (5) in the vicinity of one end (3) of the needle for holding the needle (12) and incorporating a vent passage providing fluid communication between the hollow interior of the needle (12) and the atmosphere, and sterilizing means (20) in the vicinity of the other end (4) of the shield (2), including a body of absorbent material for impregnation with a sterilizing substance, the two ends (3, 4) of the shield (2) being reciprocable relative to one another in the direction of the length of the needle (12), whereby, in use, when venting of the container is effected by placing said other end (4) of the shield (2) against the sealing portion with the shield (2) in an extended condition and applying pressure to the device in a direction towards the sealing portion, the tip of the needle (12) moves through the sterilizing means (20) and passes through the sealing portion to vent the container as the shield (2) collapses under the applied pressure.

14. A venting device for venting the interior of a sealed container by passing the tip of a hollow needle through a sealing portion of the container, the device comprising a collapsible shield (2) for shielding the needle (12), a needle support (5) in the vicinity of one end (3) of the needle for holding the needle (12) and incorporating a vent passage providing fluid communication between the hollow interior of the needle (12) and the atmosphere, and sterilizing means (20) in the vicinity of the other end (4) of the shield (2), wherein the sterilizing means (20) includes an enclosure (23) having an end wall (22) which is adapted to have an integral removable portion (25) separated therefrom by rupturing the material of the end wall (22) in a predetermined region so as to form an aperture (26) in the end wall (22) through which the tip of the needle (12) may pass, the two ends (3, 4) of the shield (2) being reciprocable relative to one another in the direction of the length of the needle (12), whereby, in use, when venting of the container is effected by placing said other end (4) of the shield (2) against the sealing portion with the shield (2) in an extended condition and applying pressure to the device in a direction towards the sealing portion, the tip of the needle (12) moves through the sterilizing means (20) and passes through the sealing portion to vent the container as the shield (2) collapses under the applied pressure.

* * * * *